(12) United States Patent
Salla et al.

(10) Patent No.: US 7,359,535 B2
(45) Date of Patent: Apr. 15, 2008

(54) SYSTEMS AND METHODS FOR RETROSPECTIVE INTERNAL GATING

(75) Inventors: Prathyusha K. Salla, Waukesha, WI (US); Gopal B. Avinash, New Berlin, WI (US); Saad Ahmed Sirohey, Pewaukee, WI (US); Tin-Su Pan, Brookfield, WI (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 782 days.

(21) Appl. No.: 10/600,107

(22) Filed: Jun. 20, 2003

(65) Prior Publication Data
US 2004/0258286 A1    Dec. 23, 2004

(51) Int. Cl.
*G06K 9/00* (2006.01)

(52) U.S. Cl. .......................... 382/128; 382/255; 378/4

(58) Field of Classification Search ................ 382/128, 382/129, 130, 131, 132, 133, 168, 172, 181, 382/232, 260, 274, 285, 291, 296, 305, 318, 382/100, 106, 107, 203, 219, 237, 254, 255, 382/276; 600/427, 413, 450; 378/4, 21
See application file for complete search history.

(56) References Cited

U.S. PATENT DOCUMENTS

| | | | | |
|---|---|---|---|---|
| 5,871,019 | A * | 2/1999 | Belohlavek | 600/450 |
| 6,144,874 | A * | 11/2000 | Du | 600/413 |
| 6,298,260 | B1 * | 10/2001 | Sontag et al. | 600/413 |
| 6,501,981 | B1 * | 12/2002 | Schweikard et al. | 600/427 |
| 6,522,712 | B1 * | 2/2003 | Yavuz et al. | 378/4 |
| 6,539,074 | B1 * | 3/2003 | Yavuz et al. | 378/4 |
| 6,556,695 | B1 * | 4/2003 | Packer et al. | 382/128 |

* cited by examiner

*Primary Examiner*—Seyed Azarian
(74) *Attorney, Agent, or Firm*—Armstrong Teasdale LLP

(57) ABSTRACT

A method for retrospective internal gating is described. The method includes acquiring images at multiple z-locations $z_1 \ldots z_n$ and at different times $t_1 \ldots t_n$ at each of the z-locations, and reordering the images at least one of the z-locations to obtain a synchronized image set.

25 Claims, 15 Drawing Sheets

SYSTEMS AND METHODS FOR RETROSPECTIVE INTERNAL GATING

BACKGROUND OF THE INVENTION

This invention relates generally to imaging systems and methods and more particularly to systems and methods for retrospective internal gating.

As a patient undergoes an imaging procedure, it is useful that the patient remain still. If a patient moves during the imaging procedure, the image may be blurred and thus lack clarity. For example, when an image is taken of a patient's chest or diaphragm area with a helical scan procedure as the patient breathes, the image lacks clarity. As another example, due to the respiratory motion of the patient, images of tumors or other areas of concern disposed within the patient's chest or abdomen tend to be blurred and lack clarity such that the tumor or area tends to appear larger or smaller than its actual size thus may render an inaccurate estimate of a size of a tumor.

Sometimes radiation therapy is used to treat a tumor. In radiation therapy, the area in which the tumor is located is exposed to a dose of radiation so as to irradiate the tumor. In order to lessen the chance of radiating normal tissue surrounding the tumor, it is useful to accurately locate the position of the tumor. This may be accomplished by imaging the tumor and the area surrounding the tumor using an imaging device such as a computed tomography (CT) imaging system, a Flouroscope, a magnetic resonance imaging (MRI) system and/or a positron emission tomography (PET) imaging system.

Although a helical CT scan can cover a typical scanning distance, for example, 20-30 cm, during a normal breathe hold, and thus completely scan the tumor during this breathe hold, the radiation therapy is a relatively long process and takes around 15 minutes. Therefore, it is not possible for the patient to hold his or her breathe during the therapy procedure. When the patient breathes, the internal organs move by as much as several centimeters, causing the tumors to move in and out of a radiation treatment field.

CT perfusion is another examination that requires an accurate image registration to compensate for the respiratory motion during the study. For example, during a CT liver perfusion procedure two types of image scans are typically performed, an arterial phase and a venous phase. The arterial phase of the imaging procedure normally produces images once a second for the first thirty seconds of breath hold time during which a contrast injection is administered to the patient. The venous phase of the imaging procedure is then performed and is normally measured in an interval of five to ten second intervals and may have a total image acquisition time of two to three minutes or longer. Because the arterial phase of the imaging procedure only takes approximately thirty seconds, holding the patient's breath can reduce or eliminate any image artifacts due to respiratory motion. However, because the venous phase may take a couple of minutes or longer, some patients may not be able to hold their breath for the entire venous phase and image artifacts may be in images obtained.

One method to address respiratory motion of the patient during imaging and application of a radiation dose is respiratory gating. In respiratory gating, movement during imaging is tracked, and even more tightly shaped conformal dose distribution is used. Respiratory gating allows therapists to track the patient's respiratory cycle both at the time of the CT scan for imaging and at the time of treatment. In effect, respiratory gating facilitates isolation of the position of the target during one specific phase of the respiratory cycle, generally, during either exhale or inhale. Thus, by isolating the target position, therapists can decrease the size of the radiation fields to closely match the target size and position.

Respiratory gating is accomplished by monitoring the patient's normal breathing pattern. For example, in a known method, every time the patient exhales, the radiation beam comes on instantly for half a second. The moment the patient starts to inhale, the radiation beam is terminated. The radiation beam is pulsed repeatedly in such a manner until the entire radiation dose has been delivered. Unfortunately, such a configuration increases the total time of radiation treatment.

BRIEF DESCRIPTION OF THE INVENTION

In one aspect, a method for retrospective internal gating is described. The method includes acquiring images at multiple z-locations $z_1 \ldots z_n$ and at different times $t_1 \ldots t_n$ at each of the z-locations, and reordering the images at least one of the z-locations to obtain a synchronized image set.

In another aspect, a computer-readable medium encoded with a program is described. The program is configured to acquire images at multiple z-locations $z_1 \ldots z_n$ and at different times $t_1 \ldots t_n$ at each of the z-locations, and reorder the images at at least one of the z-locations to obtain a synchronized image set.

In yet another aspect, a computer is described. The computer is configured to acquire images at multiple z-locations $z_1 \ldots z_n$ and at different times $t_1 \ldots t_n$ at each of the z-locations, and reorder the images at at least one of the z-locations to obtain a synchronized image set.

In still another aspect, an imaging system is described. The imaging system includes a scanner configured to generate attenuation data by scanning an object, and a controller electrically coupled to the scanner. The controller is configured to acquire images at multiple z-locations $z_1 \ldots z_n$ and at different times $t_1 \ldots t_n$ at each of the z-locations, and reorder the images at at least one of the z-locations to obtain a synchronized image set.

In another aspect, a computed tomography (CT) imaging system is described. The CT imaging system includes a CT scanner to generate attenuation data by scanning an object, and a controller electrically coupled to the CT scanner. The controller is configured to acquire CT images at multiple z-locations $z_1 \ldots z_n$ and at different times $t_1 \ldots t_n$ at each of the z-locations, and reorder the CT images at at least one of the z-locations to obtain a synchronized image set.

DETAILED DESCRIPTION OF THE INVENTION

Figure 1:
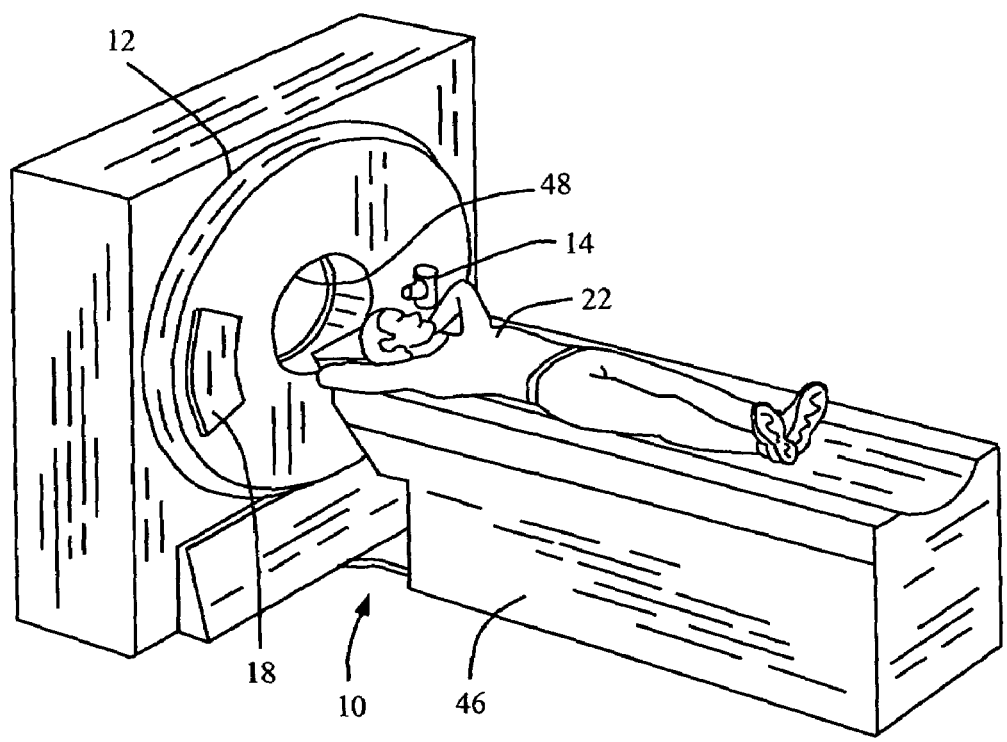
FIG. 1 is a pictorial view of a CT imaging system in which systems and methods for retrospective internal gating are implemented.

In computed tomography (CT) imaging system configurations, an X-ray source projects a fan-shaped beam which is collimated to lie within an X-Y plane of a Cartesian coordinate system and generally referred to as an "imaging plane". The X-ray beam passes through an object being imaged, such as a patient. The beam, after being attenuated by the object, impinges upon an array of radiation detectors. The intensity of the attenuated radiation beam received at the detector array is dependent upon the attenuation of an X-ray beam by the object. Each detector element of the array produces a separate electrical signal that is a measurement of the beam intensity at the detector location. The intensity measurements from all of the detectors are acquired separately to produce a transmission profile.

In third generation CT systems, the X-ray source and the detector array are rotated with a gantry within the imaging plane and around the object to be imaged such that the angle at which the X-ray beam intersects the object constantly changes. A group of X-ray attenuation measurements, i.e., projection data, from the detector array at one gantry angle is referred to as a "view". A "scan" of the object comprises a set of views made at different gantry angles, or view angles, during one revolution of the X-ray source and detector.

In an axial scan, the projection data is processed to construct an image that corresponds to a 2-dimensional (2D) slice taken through the object. One method for reconstructing an image from a set of projection data is referred to in the art as the filtered back projection technique. This process converts the attenuation measurements from a scan into integers called "CT numbers" or "Hounsfield units", which are used to control the brightness of a corresponding pixel on a cathode ray tube display. Positron emission tomography (PET) scanners incorporate a process similar to that found in CT, in that a map or the object attenuation can be generated. A method to perform this attenuation measurement includes use of rotation rod sources containing positron-emitting radionuclides. The rods rotate outside the patient bore, but inside the diameter of the PET detector ring. Annihilation events occurring in the rods can send one photon into a near-side detector while the pair photon traverses the object of interest in a manner similar to the CT X-ray. The data found from this method contains essentially the same information as that found from the CT method except for the statistical quality of the resultant data. In the rotating rod case, the statistical quality is orders of magnitude inferior to most common CT scans. For the PET purpose, data acquired in this manner is used to correct for the attenuation seen in the object by the 511 keV photons, which is often the most substantial correction performed on the PET data.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two dimensional slice taken through the object.

At least some CT systems are configured to also perform Positron Emission Tomography (PET) and are referred to as PET-CT systems. Positrons are positively charged electrons (anti-electrons) which are emitted by radio nuclides that have been prepared using a cyclotron or other device. The radionuclides most often employed in diagnostic imaging are fluorine-18 ($^{18}F$), carbon-11 ($^{11}C$), nitrogen-13 ($^{13}N$), and oxygen-15 ($^{15}O$). Radionuclides are employed as radioactive tracers called "radiopharmaceuticals" by incorporating them into substances such as glucose or carbon dioxide. One common use for radiopharmaceuticals is in the medical imaging field.

To use a radiopharmaceutical in imaging, the radiopharmaceutical is injected into a patient and accumulates in an organ, which is to be imaged. It is known that specific radiopharmaceuticals become concentrated within certain organs. The process of concentrating often involves processes such as glucose metabolism, fatty acid metabolism and protein synthesis.

After the radiopharmaceutical becomes concentrated within an organ and while the radionuclides decay, the radionuclides emit positrons. The positrons travel a very short distance before they encounter an electron and, when the positron encounters an electron, the positron is annihilated and converted into two photons, or gamma rays. This annihilation event is characterized by two features which are pertinent to medical imaging and particularly to medical imaging using PET. First, each gamma ray has an energy of approximately 511 keV upon annihilation. Second, the two gamma rays are directed in nearly opposite directions.

In PET imaging, if the general locations of annihilations can be identified in three dimensions, a 3-dimensional (3D) image of radiopharmaceutical concentration in an organ can be reconstructed for observation. To detect annihilation locations, a PET camera is employed. An exemplary PET camera includes a plurality of detectors and a processor which, among other things, includes coincidence detection circuitry.

The coincidence circuitry identifies essentially simultaneous pulse pairs which correspond to detectors which are essentially on opposite sides of the imaging area. Thus, a simultaneous pulse pair indicates that an annihilation has occurred on a straight line between an associated pair of detectors. Over an acquisition period of a few minutes millions of annihilations are recorded, each annihilation associated with a unique detector pair. After an acquisition period, recorded annihilation data can be used via any of several different well known image reconstruction methods to reconstruct the 3D image of the organ.

As used herein, an element or step recited in the singular and preceded with the word "a" or "an" should be understood as not excluding plural the elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate (or are configured to generate) at least one viewable image.

Figure 2:
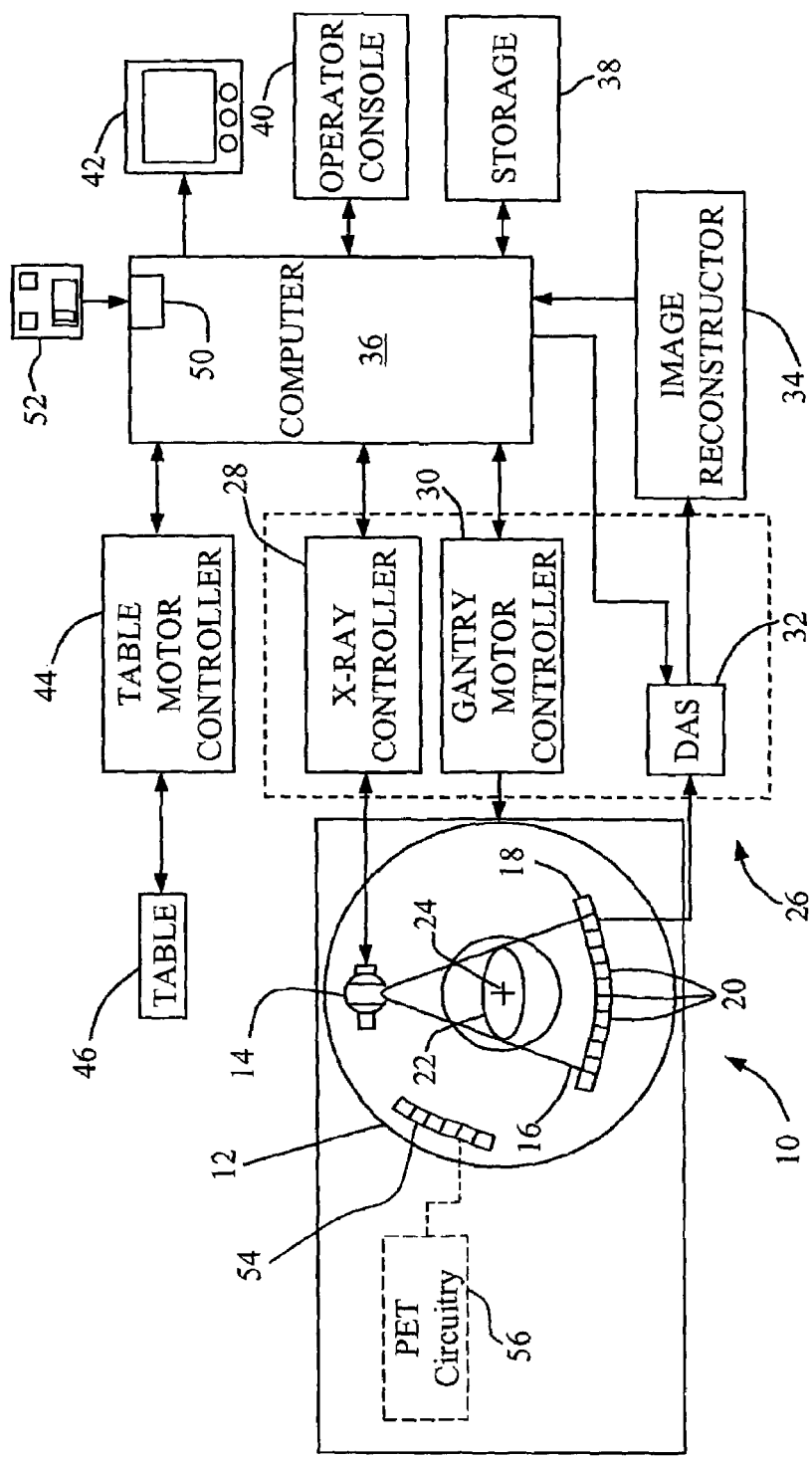
FIG. 2 is a block schematic diagram of the CT imaging system illustrated in FIG. 1.

Referring to FIGS. 1 and 2, a multi-slice scanning imaging system, for example, a CT imaging system 10, is shown as including a gantry 12 representative of a "third generation" CT imaging system. Gantry 12 has an X-ray source 14 that projects a beam of X-rays 16 toward a detector array 18 on the opposite side of gantry 12. Detector array 18 is formed by a plurality of detector rows (not shown) including a plurality of detector elements 20 which together sense the projected X-rays that pass through an object, such as a medical patient 22. Each detector element 20 produces an electrical signal that represents the intensity of an impinging X-ray beam and hence allows estimation of the attenuation of the beam as it passes through object or patient 22. During a scan to acquire X-ray projection data, gantry 12 and the components mounted thereon rotate about a center of rotation 24.

FIG. 2 shows only a detector row of detector elements 20. However, multislice detector array 18 includes a plurality of parallel detector rows of detector elements 20 such that projection data corresponding to a plurality of quasi-parallel or parallel slices can be acquired simultaneously during a scan.

Rotation of gantry 12 and the operation of X-ray source 14 are governed by a control mechanism 26 of CT system 10. Control mechanism 26 includes an X-ray controller 28 that provides power and timing signals to X-ray source 14 and a gantry motor controller 30 that controls the rotational speed and position of gantry 12. A data acquisition system (DAS) 32 in control mechanism 26 samples analog data from detector elements 20 and converts the data to digital signals for subsequent processing. An image reconstructor 34 receives sampled and digitized X-ray data from DAS 32 and performs high-speed image reconstruction. The reconstructed image is applied as an input to a computer 36 which stores the image in a storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, X-ray controller 28 and gantry motor controller 30. In addition, computer 36 operates a table motor controller 44 which controls a motorized table 46 to position patient 22 in gantry 12. Particularly, table 46 moves portions of patient 22 through gantry opening 48.

In one embodiment, computer 36 includes a device 50, for example, a floppy disk drive or CD-ROM drive, for reading instructions and/or data from a computer-readable medium 52, such as a floppy disk or CD-ROM. In another embodiment, computer 36 executes instructions stored in firmware (not shown). Computer 36 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

Although the specific embodiment mentioned above refers to a third generation CT system, methods for analyzing an abnormality of an object equally apply to fourth generation CT systems that have a stationary detector and a rotating X-ray source, fifth generation CT systems that have a stationary detector and an X-ray source.

Additionally, although the herein described methods are described in a medical setting, it is contemplated that the benefits of the methods accrue to non-medical imaging systems such as those systems typically employed in an industrial setting or a transportation setting, such as, for example, but not limited to, a baggage scanning system for an airport, other transportation centers, government buildings, office buildings, and the like. The benefits also accrue to micro PET and CT systems which are sized to study lab animals as opposed to humans.

It is noted that CT imaging system can be combined with a PET imaging system, that is described below, to form a PET-CT imaging system. In one embodiment, the PET-CT imaging system includes a plurality of PET detectors 54, rotating rod sources (not shown) and a PET circuitry 56 within gantry 12. An example of such as PET-CT system is a Discovery LS PET-CT system commercially available from General Electric Medical Systems, Waukesha, Wis. In another embodiment, the PET-CT imaging system includes the plurality of PET detectors 54 and PET circuitry 56 located with a separate gantry. An example of such a PET-CT system is a Discovery ST system commercially available from General Electric Medical Systems.

Figure 3:
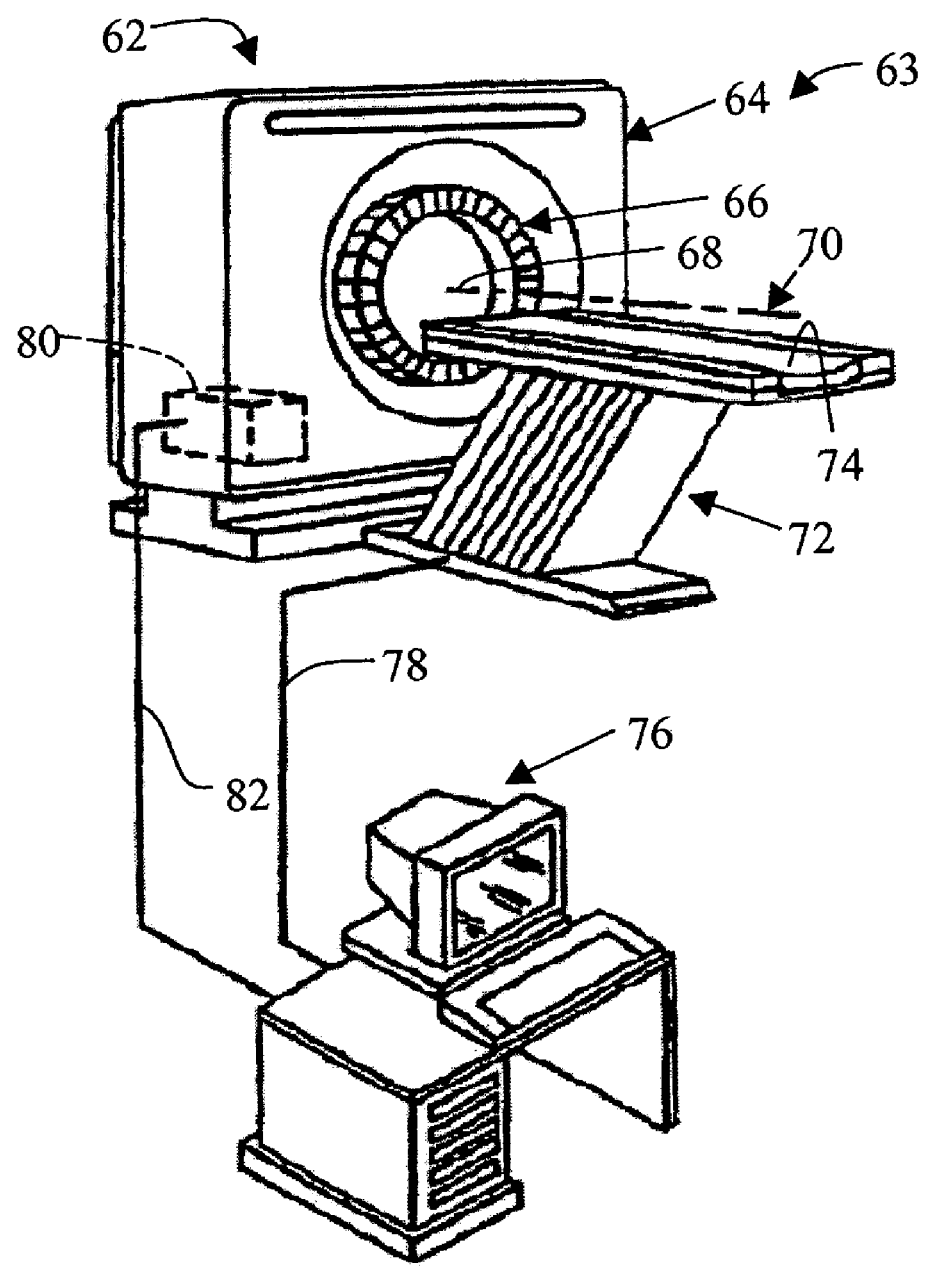
FIG. 3 is a perspective view of an embodiment of a PET imaging system.

FIG. 3 is a perspective view of an embodiment of a PET imaging system 62. PET imaging system 62 includes a PET scanner 63. PET scanner 63 includes a gantry 64 which supports a detector ring assembly 66 about a central opening, or bore 68. Detector ring assembly 66 is circular in shape, and is made up of multiple detector rings (not shown) that are spaced along a central axis 70 to form a cylindrical detector ring assembly. A table 72 is positioned in front of gantry 66 and is aligned with central axis 70 of detector ring assembly. A table controller (not shown) moves a table bed 74 into bore 68 in response to commands received from an operator work station 76 through a serial communications link 78. A gantry controller 80 is mounted within gantry 64 and is responsive to commands received from operator work station 76 through a second serial communication link 82 to operate gantry 64.

Figure 4:
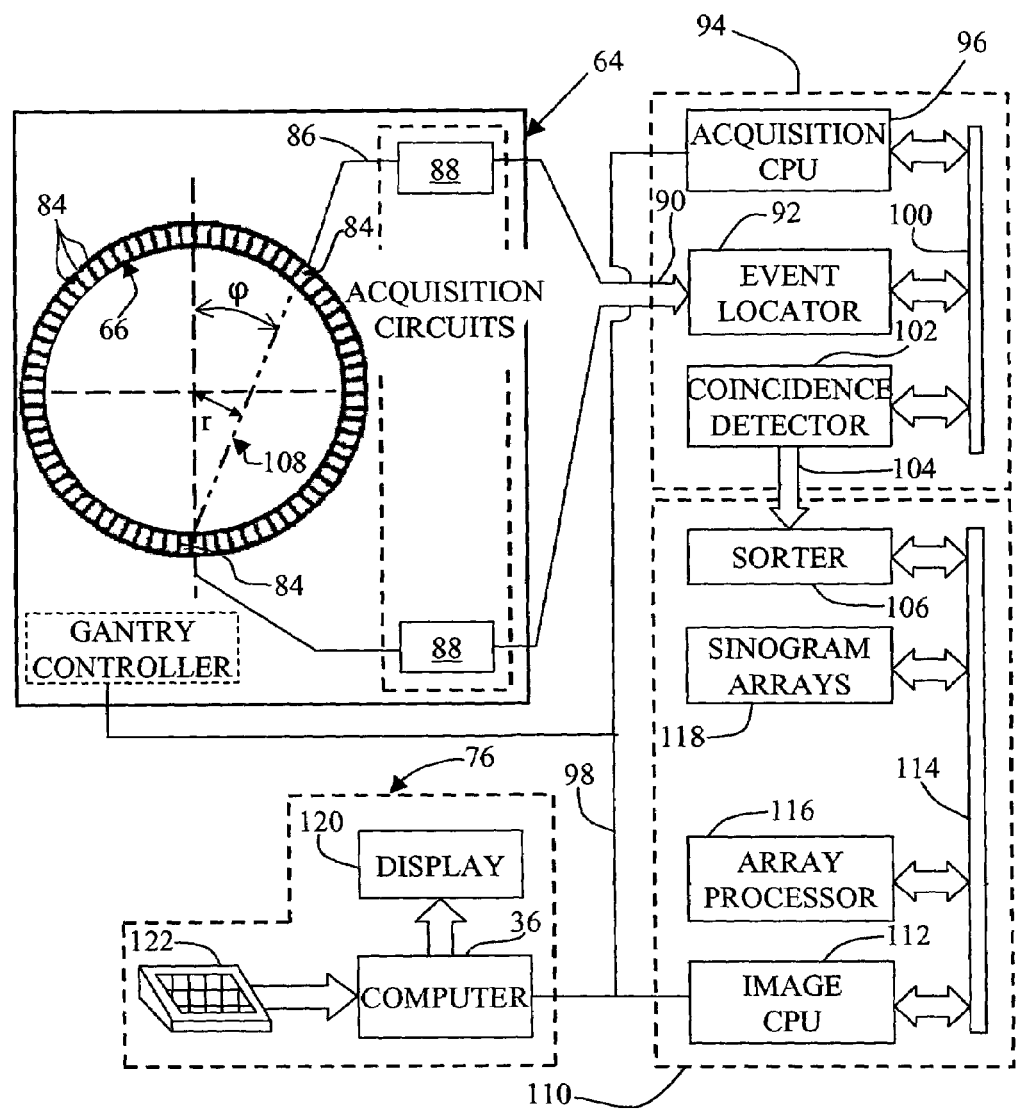
FIG. 4 is a block diagram of the PET imaging system of FIG. 3.

FIG. 4 shows a block diagram of PET imaging system 62 of FIG. 3. Each detector ring of detector ring assembly 66 includes detectors 84. Each detector 84 includes scintillator crystals (not shown). Each scintillator crystal is disposed in front of a photomultiplier tube (PMT) (not shown). The PMTs produce analog signals on a line 86 when a scintillation event occurs at one of the scintillator crystals that are disposed in front of the PMTs. The scintillation event occurs when a photon is received by one of the scintillator crystals. In one embodiment, photons are generated by administering a compound, such as, $^{11}$C-labeled glucose, $^{18}$F-labeled glucose, $^{13}$N-labeled ammonia and $^{15}$O-labeled water within the object, an emission of positrons by the compounds, a collision of the positrons with free electrons of the object, and generation of simultaneous pairs of photons. Alternatively, the photons are transmitted by rotating rod sources within a FOV of PET imaging system 62. A set of acquisition circuits 88 is mounted within gantry 64 to receive the signals and produce digital signals indicating event coordinates (x, y) and total energy. These are sent through a cable 90 to an event locator circuit 92 housed in a separate cabinet. Each acquisition circuit 88 also produces an event detection pulse (EDP) which indicates the exact moment the scintillation event took place.

Event locator circuits 92 form part of a data acquisition processor 94 which periodically samples the signals produced by acquisition circuits 88. Processor 94 has an acquisition central processing unit (CPU) 96 which controls communications on a local area network 98 and a backplane bus 100. Event locator circuits 92 assemble the information regarding each valid event into a set of digital numbers that indicate precisely when the event took place and the position of a scintillation crystal which detected the event. This event data packet is conveyed to a coincidence detector 102 which is also part of data acquisition processor 94. Coincidence detector 102 accepts the event data packets from event locators 92 and determines if any two of them are in coincidence. Events which cannot be paired are discarded, but coincident event pairs are located and recorded as a coincidence data packet that is conveyed through a serial link 104 to a sorter 106.

Each pair of event data packets that is identified by coincidence detector 102 is described in a projection plane format using four variables r, v, θ, and Φ. Variables r and Φ identify a plane 108 that is parallel to central axis 70, with Φ specifying the angular direction of the plane with respect to a reference plane and r specifying the distance of the central axis from the plane as measured perpendicular to the plane. Variables v and θ (not shown) further identify a particular line within plane 108, with θ specifying the angular direction of the line within the plane, relative to a reference line within the plane, and v specifying the distance of center from the line as measured perpendicular to the line.

Sorter 106 forms part of an image reconstruction processor 110. Sorter 106 counts all events occurring along each projection ray, and stores that information in the projection plane format. Image reconstruction processor 110 also includes an image CPU 112 that controls a backplane bus 114 and links it to local area network 98. An array processor 116 also connects to backplane bus 114. Array processor 116 converts the event information stored by sorter 106 into a 2D sinogram array 118. Array processor 116 converts data, such as, for instance, emission data that is obtained by emission of positrons by the compound or transmission data that is obtained by transmission of photons by the rotating rod sources, from the projection plane format into the 2D sinogram format. Examples of the 2D sinogram include a PET emission sinogram that is produced from emission data and a PET transmission sinogram that is produced from transmission data. Upon conversion of the data into the two-dimensional sinogram format, images can be constructed. Operator work station 76 includes computer 36, a cathode ray tube (CRT) display 120, and a keyboard 122. Computer 36 connects to local area network 98 and scans keyboard 122 for input information. Through keyboard 122 and associated control panel switches, the operator controls calibration of PET imaging system 62, its configuration, and positioning of table 72 for a PET scan. Similarly, once computer 36 receives a PET image and a CT image, the operator controls display of the images on CRT display 120. On receipt of the CT images, computer 36 performs a method for retrospective internal gating.

Figure 5:
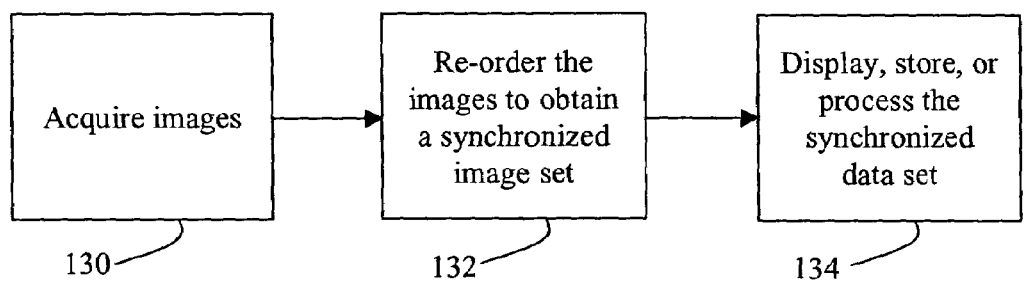
FIG. 5 is a flowchart of an embodiment of a method for retrospective internal gating.
Figure 6:
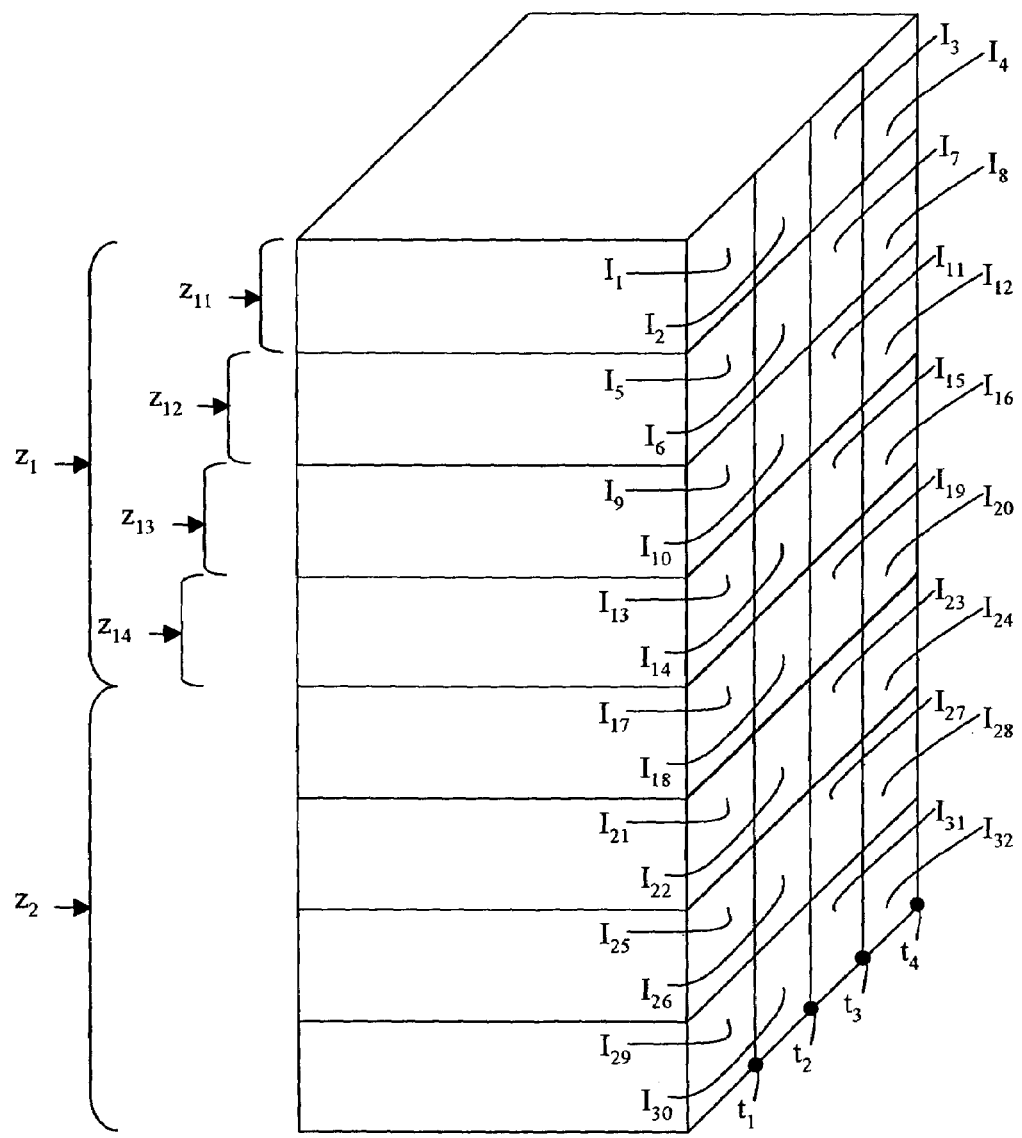
FIG. 6 shows 4-dimensional (4D) image data that is acquired at z-locations to execute the method of FIG. 5.
Figure 7:
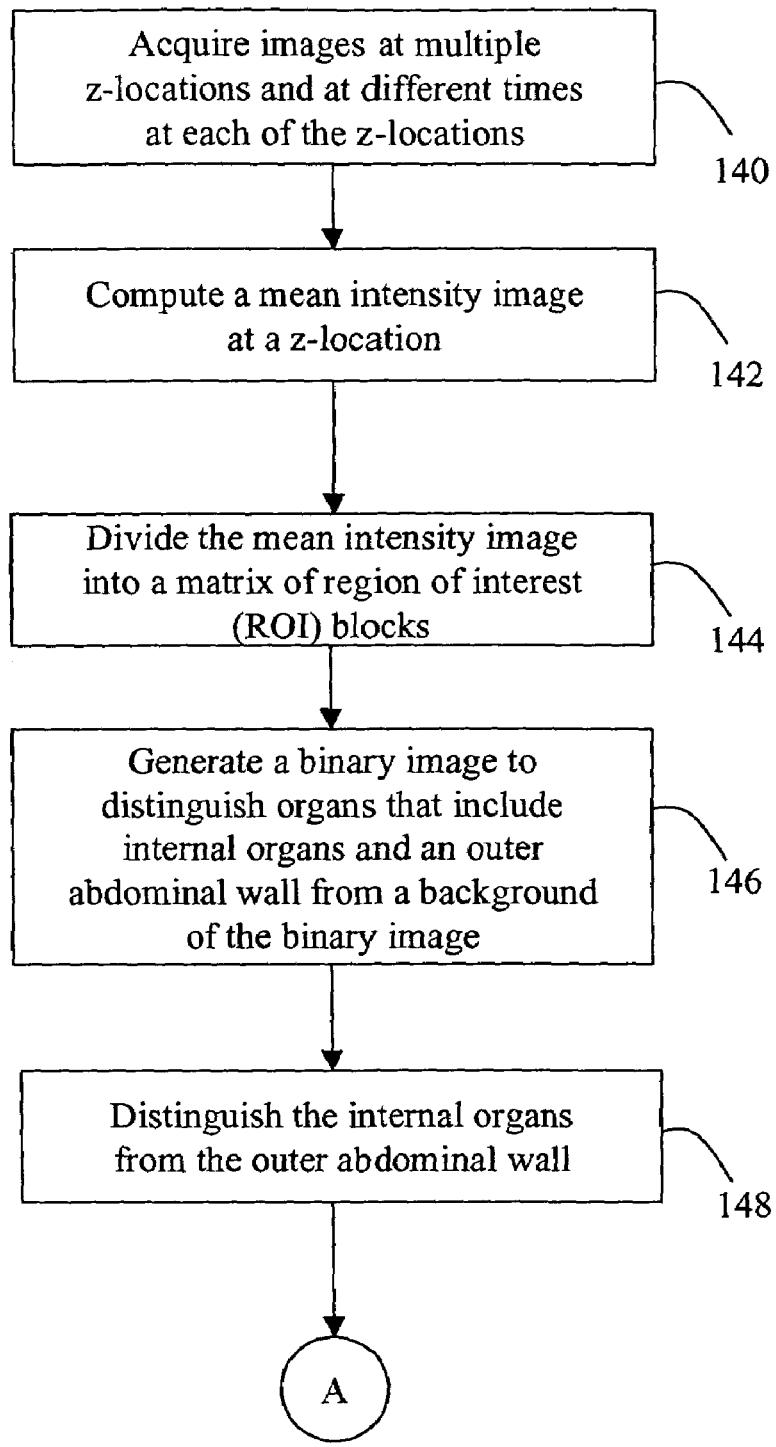
FIGS. 7-10 is a flowchart of another embodiment of a method for retrospective internal gating.
Figure 8:
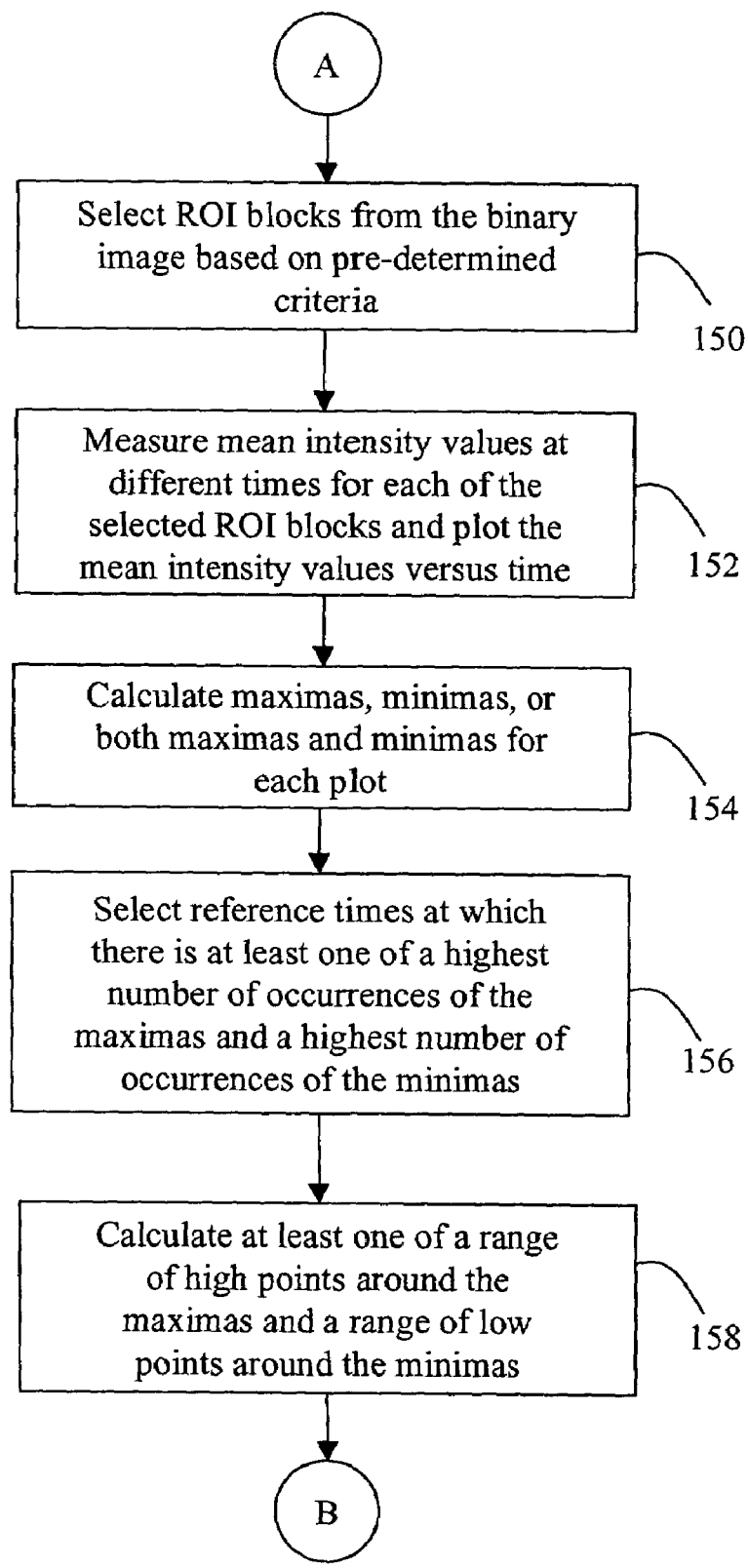
Figure 9:
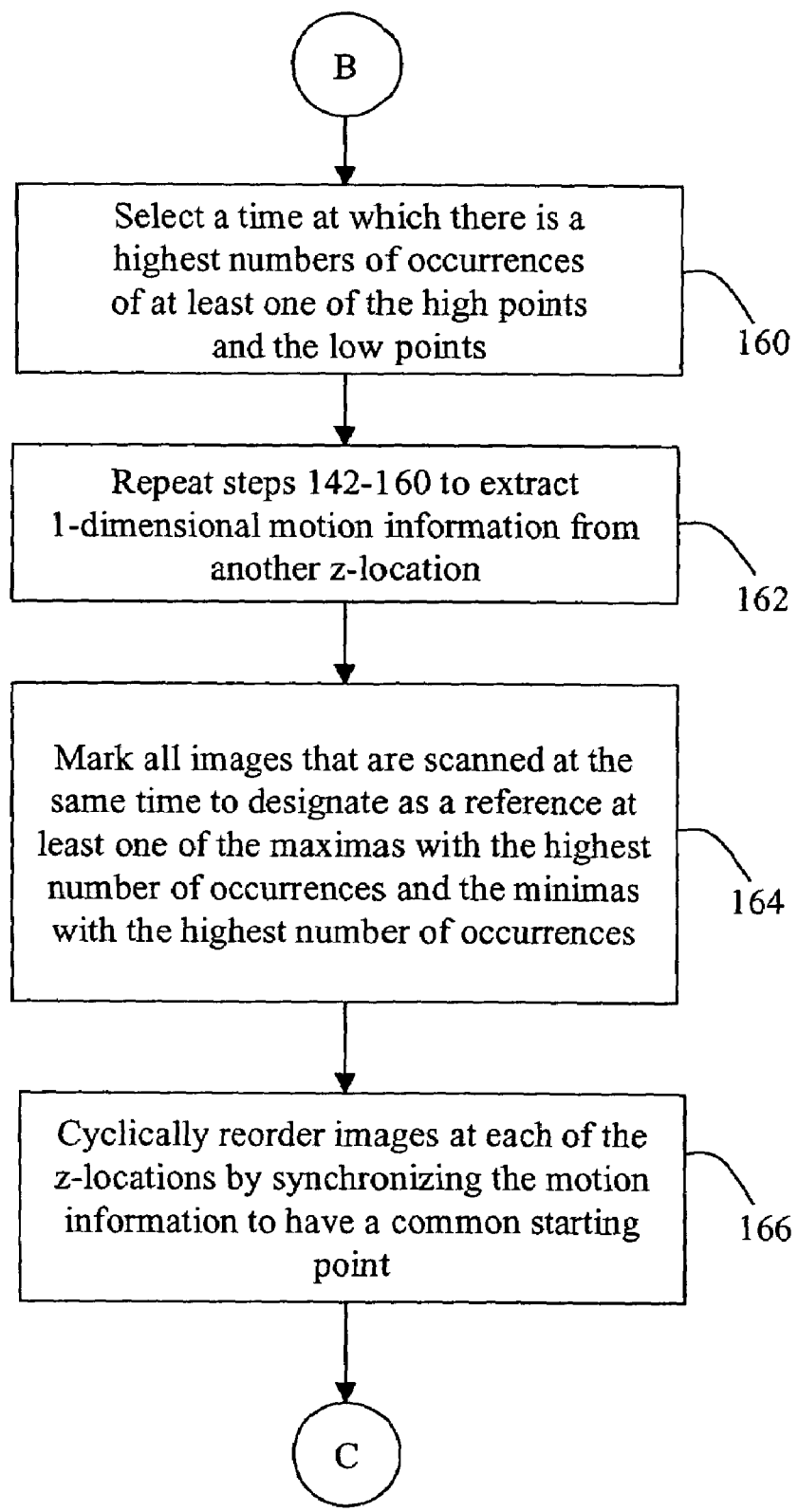
Figure 10:
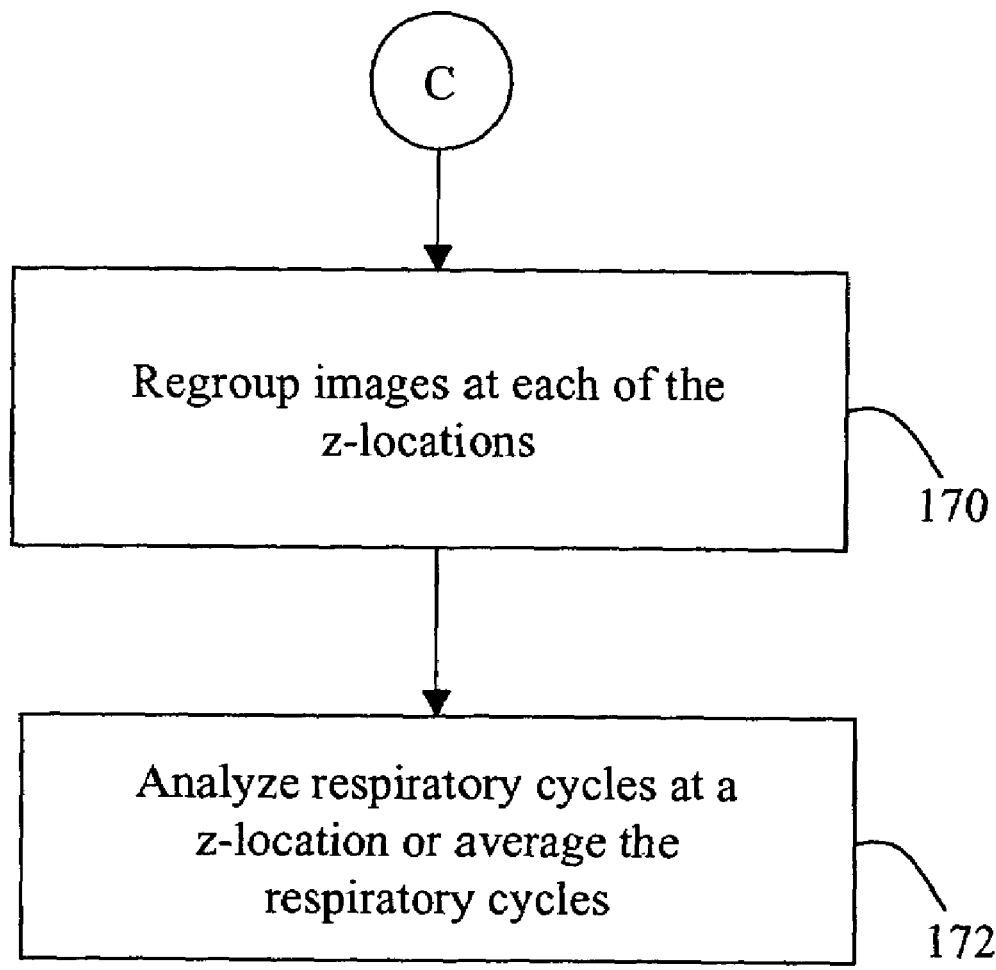
Figure 11:
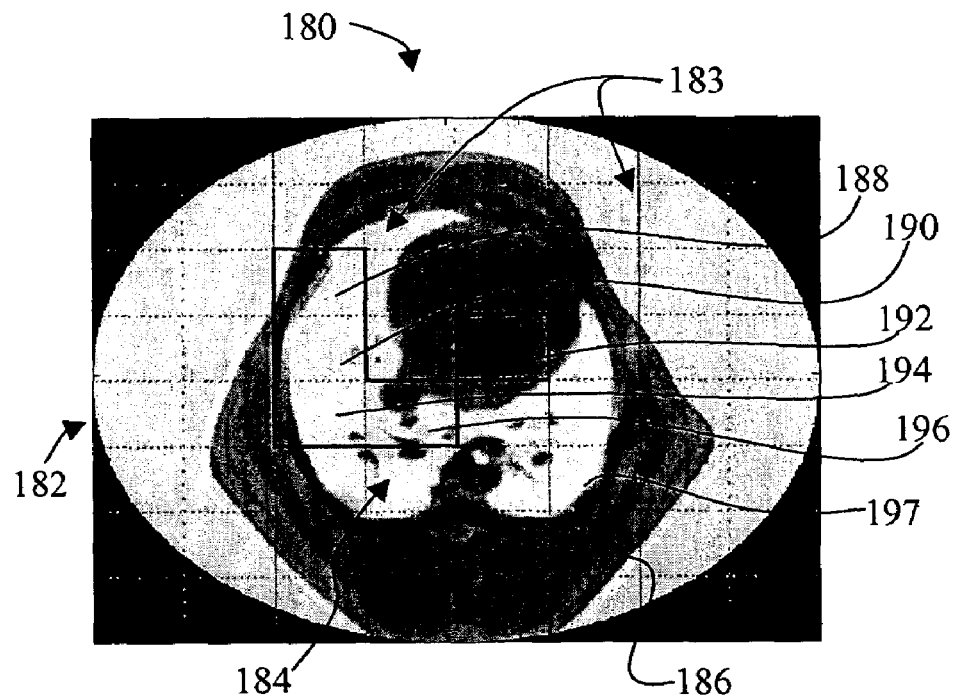
FIG. 11 shows a mean intensity image and plots of intensities versus time, which are obtained during the method of FIGS. 7-9.
Figure 11:
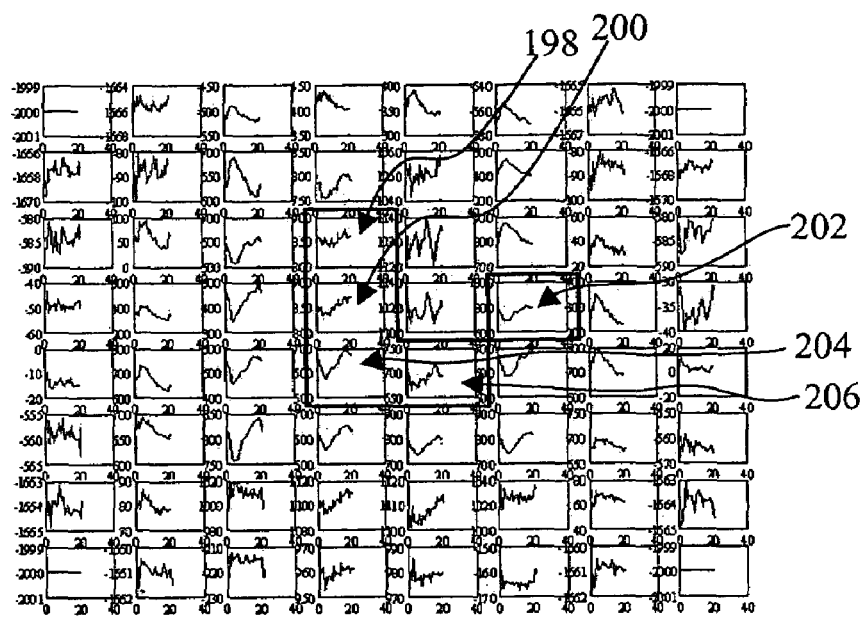
Figure 12:
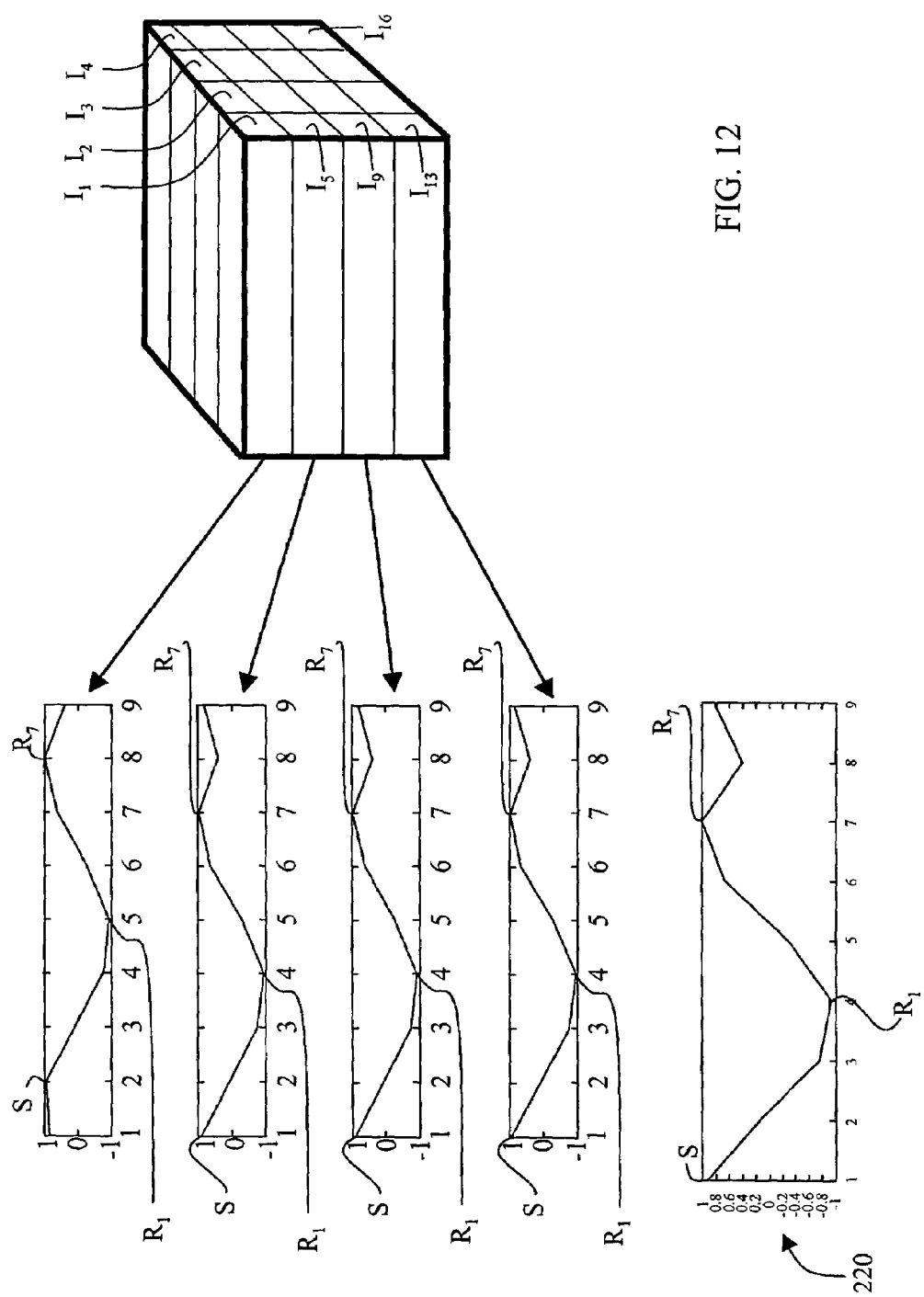
FIG. 12 shows respiratory cycles that are obtained during the method of FIGS. 7-9.

FIGS. 5 and 6 illustrate an embodiment of a method for retrospective internal gating. The method includes acquiring 130 images $I_1 \ldots I_{32}$ or slices at multiple z-locations $z_1 \ldots z_2$ and at different times $t_1 \ldots t_4$ at each of the z-locations, and reordering 132 images at at least one of z-locations $z_1 \ldots z_2$ to obtain a synchronized image set. Images $I_1 \ldots I_{16}$ are acquired by using a $3^{rd}$ generation CT scanner having 4 detector arrays. As an example, at z-location $z_1$, multiple images $I_1, I_5, I_9$, and $I_{13}$ are acquired at time $t_1$. In another embodiment, images $I_1 \ldots I_{16}$ are acquired, in a cine acquisition mode, during a period of time including a respiratory cycle of patient 22 lasting, for instance, between 3 and 6 seconds and a two-third gantry rotation lasting, for instance, 0.33 seconds. In yet another embodiment, images $I_1 \ldots I_{16}$ are acquired, in a cine acquisition mode, for a period of time including a respiratory cycle of patient 22 and a complete gantry rotation lasting 0.5 seconds. Images $I_1 \ldots I_{32}$ include a 4-dimensional (4D) image data set. In an alternative embodiment, there are more or less z-locations than shown in FIG. 6. In yet another alternative embodiment, images can be acquired for more than 4 times $t_1 \ldots t_4$ at each z-location. In still another alternative embodiment, a detector with 8 detector arrays is used in a cine acquisition mode to acquire images. The method also includes displaying 134 the synchronized data set on display 42, storing 134 the synchronized data set in storage 38, or processing 134 the synchronized data set.

FIGS. 7, 8, 9, 10, 11, and 12 illustrate an embodiment of the method of FIGS. 5 and 6. The method includes acquiring 140 images $I_1 \ldots I_{32}$ at multiple z-locations $z_1 \ldots z_2$ and at different times $t_1 \ldots t_4$ at each of the z-locations. The method further includes extracting 1-dimensional (1D) motion information from images $I_1 \ldots I_{16}$ by using temporal image data acquired at different times $t_1 \ldots t_4$ at z-location $z_1$. Examples of motion information include respiratory motion information and cardiac motion information. Motion information is extracted from images $I_1 \ldots I_{16}$ by computing 142 a mean intensity image 180 from images $I_1 \ldots I_{16}$. The motion information is further extracted by dividing 144 mean intensity image 180 into an 8×8 matrix 182 of blocks of a desired size of region of interest (ROI). Alternatively, mean intensity image 180 is divided into other matrix sizes, such as, for instance, 5×5, 6×8, 9×10, and 12×12, based on the desired ROI size.

The motion information is also extracted by generating 146 a binary image (not shown) to distinguish organs of patient 22 that are imaged from a background 183 of the binary image. For example, the organs correspond to a CT Hounsfield number "1" and background 183 corresponds to a CT Hounsfield number "0". The organs include internal organs 184, such as, for instance, livers, kidneys, lungs, and hearts. The organs also include an outer abdominal wall 186. The motion information is further extracted by distinguishing 148 internal organs 184 from outer abdominal wall 186. Internal organs 184 are distinguished from outer abdominal wall 186 by a segmentation process. The segmentation process distinguishes intensity values, such as, for instance, CT Hounsfield numbers, of internal organs 184 from intensity values of outer abdominal wall 186. Alternatively, internal organs 184 are manually distinguished from outer abdominal wall 186 and from background 183. For example, internal organs 184 are manually distinguished from outer abdominal wall 186 and from background 183 by depositing at least one seed in a pixel (not shown) of the binary image and appending neighboring pixels to the seed. The neighboring pixels have properties, such as, for instance, color, intensity, or contrast, that are similar to properties of the pixel. Pixels of internal organs 184 are labeled as "1" and pixels of outer abdominal wall 186 and background 183 are labeled as "0". Alternatively, pixels of internal organs 184 are labeled as "0" and pixels of outer abdominal wall 186 and background 183 are labeled as "1". In yet another alternative embodiment, internal organs 184 are automatically distinguished from outer abdominal wall 186 and from background 183 by connectivity and morphological operations, such as, for instance, opening, closing, erosion, and dilation. For example, after smoothing edges of each pixel of the binary image, connectivity between two elements of internal organs 184 is defined as the highest intensity for which a connecting path between the elements exists along which intensity of an element is not darker than the highest intensity. Connectivity and morphological operations are described in detail in Morphological Methods in Image and Signal processing: Charles R Giardina; Edward R. Dougherty, Prentice-Hall, Inc, 1988 and in Fundamentals of Digital Image Processing: Anil K Jain, Prentice-Hall, Inc., 1989.

The motion information is also extracted by selecting 150 ROI blocks 188, 190, 192, 194, and 196 from the binary image based on pre-determined criteria. As an example, ROI blocks 188, 190, 192, 194, and 196 are selected by distinguishing intensities of ROI blocks 188, 190, 192, 194, and 196 from intensities of remaining ROI blocks of mean intensity image 180. Intensities of ROI blocks 188, 190, 192, 194, and 196 are above a threshold, such as, for instance, 350, and intensities of ROI blocks that are not selected are below the threshold. As another example, ROI blocks 188, 190, 192, 194, and 196 are selected since they are a portion of an organ of interest and a portion of background 183. ROI blocks that selected are the ones that exceed a certain threshold as described above and are a part of an organ of interest of patient 22 and background, such as background 183. The organ of interest includes any one of internal organs 184, outer abdominal wall 186, and an inner abdominal wall 197.

The motion information is further extracted by measuring 152 mean intensity values at times $t_1 \ldots t_4$ for each of selected ROI blocks 188, 190, 192, 194, and 196 and plotting the mean intensity values as a function of times $t_1 \ldots t_4$ to provide motion information at each of selected ROIs 188, 190, 192, 194, and 196. Plots 198, 200, 202, 204, and 206 are graphs of the mean intensity values as function of times $t_1 \ldots t_4$ for selected ROIs 188, 190, 192, 194, and 196 respectively. For example, plot 198 is a graph of the mean intensity values as function of times $t_1 \ldots t_4$ for selected ROI 188. The mean intensity values are measured from temporal image data acquired at different times $t_1 \ldots t_4$ at $z_1$. The motion information is also extracted by calculating 154 maximas from plots 198, 200, 202, 204, and selecting 156 a reference time at which there is a highest number of occurrences of the maximas. Alternatively, the motion information is extracted by calculating 154 minimas from plots 198, 200, 202, 204, and 206, and selecting 156 a reference time at which there is a highest number of occurrences of the minimas. In yet another alternative embodiment, both maximas and minimas are calculated 154 and references times for highest number of occurrences of each are selected 156.

The motion information is further extracted by calculating 158 at least one of a range of high points and a range of low points for each of selected ROI blocks 188, 190, 192, 194, and 196. The range of the high points is a range of points around the maximas of selected ROI blocks 188, 190, 192, 194, and 196 and the range of low points is a range of points around the minimas of the selected ROI blocks. For example, if the maximas are 8, the range of high points is between 7 and 9. As another example, if the minimas are 3, the range of low points is between 2 and 4. The motion information is extracted by selecting 160 a time at which there is a highest number of occurrences of at least one of the high points and the low points.

The method further includes extracting 162, in a similar manner described above, 1D motion information from remaining image set of images $I_{17} \ldots I_{32}$ by using temporal image data acquired at different times $t_1 \ldots t_4$ at z-location $z_2$ and by repeating steps 142, 144, 146, 148, 150, 152, 154, 156, 158, and 160. The method further includes performing phase synchronization by marking 164 all images that are scanned at the same time to designate as a reference at least one of the maximas with the highest number of occurrences and the minimas with the highest number of occurrences. For example, images $I_1$, $I_5$, $I_9$, and $I_{13}$ that are scanned at time $t_1$ are marked to designate, as a reference "$R_7$", the maximas with the highest number of occurrences. As another example, images $I_1$, $I_5$, $I_9$, and $I_{13}$ that are scanned at time $t_1$ are marked to designate, as a reference "$R_1$", the minimas with the highest number of occurrences. Alternatively, the method includes performing phase synchronization by marking all images that are scanned at the same time to designate as a reference at least one of the high points with the highest number of occurrences and the low points with the highest number of occurrences.

The method also includes cyclically reordering 166 images $I_1 \ldots I_{32}$ at each of z-locations $z_1 \ldots z_2$ by synchronizing the motion information to have a common starting point S. For example, since images $I_1 \ldots I_4$ wrap around a respiratory cycle of object, image $I_2$ has starting point S and so images $I_1 \ldots I_4$ will be cyclically reordered from order $I_1 \ldots I_4$ to $I_2$, $I_3$, $I_4$, $I_1$. After the cyclical reordering, $I_{2\ I5}$, $I_9$, and $I_{13}$ have the same respiratory cycle 220 with starting point S. It is noted that in an alternative embodiment of the method, one or more of steps 158 and 160 may be omitted. The method includes regrouping 170 images $I_1 \ldots I_{16}$ after the cyclical reordering. For example, images $I_2$, $I_5$, $I_9$, and $I_{13}$ form a group after the cyclical reordering since images $I_2$, $I_5$, $I_9$, and $I_{13}$ appear to be taken at the same time. The method also includes regrouping 170 images $I_{17} \ldots I_{32}$ in a similar manner. The method further includes analyzing 172, as a group, respiratory cycles at a z-location, for instance, $z_1$, or averaging respiratory cycles at the z-location to represent an averaged respiratory cycle that represents motion of the organ.

Figure 13:
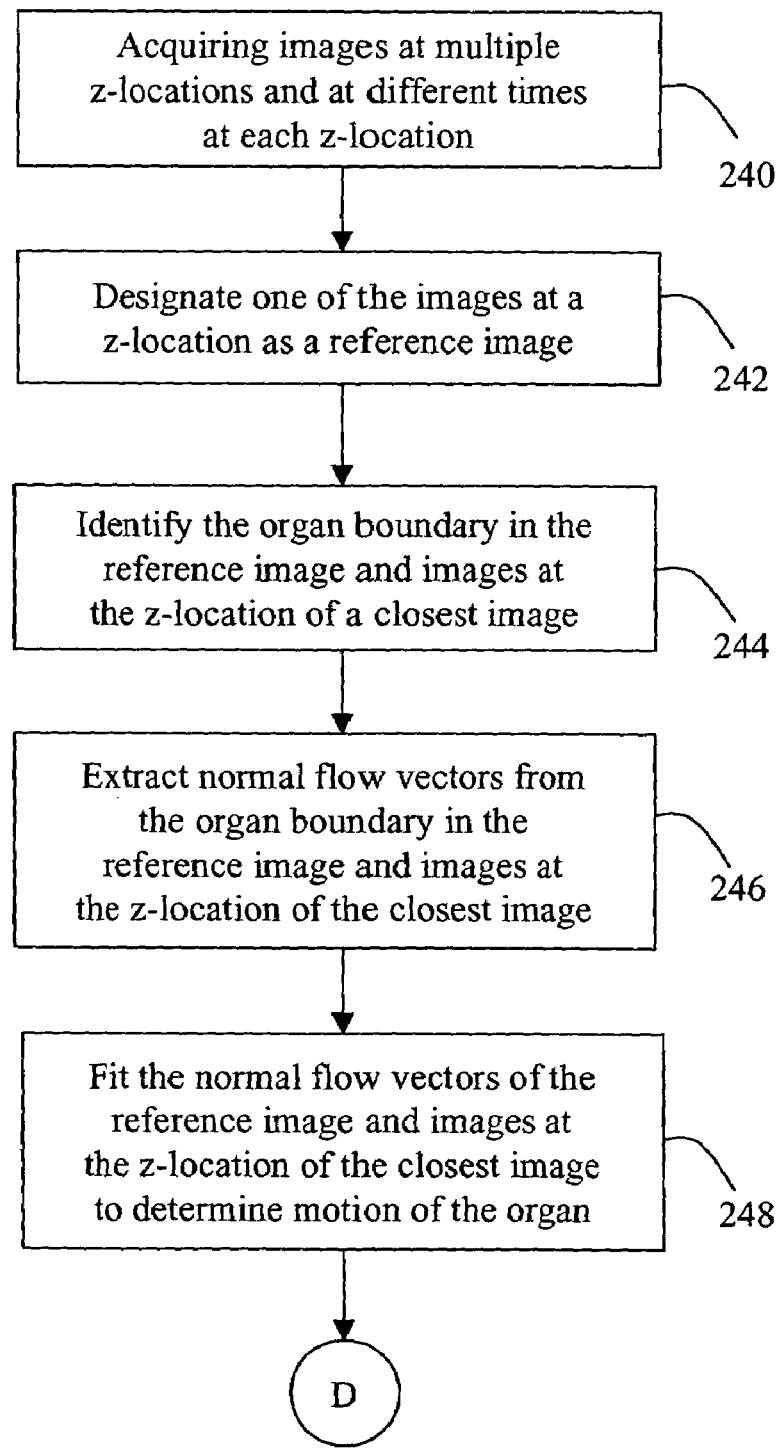
FIGS. 13 and 14 is a flowchart of yet another embodiment of a method for retrospective internal gating.
Figure 14:
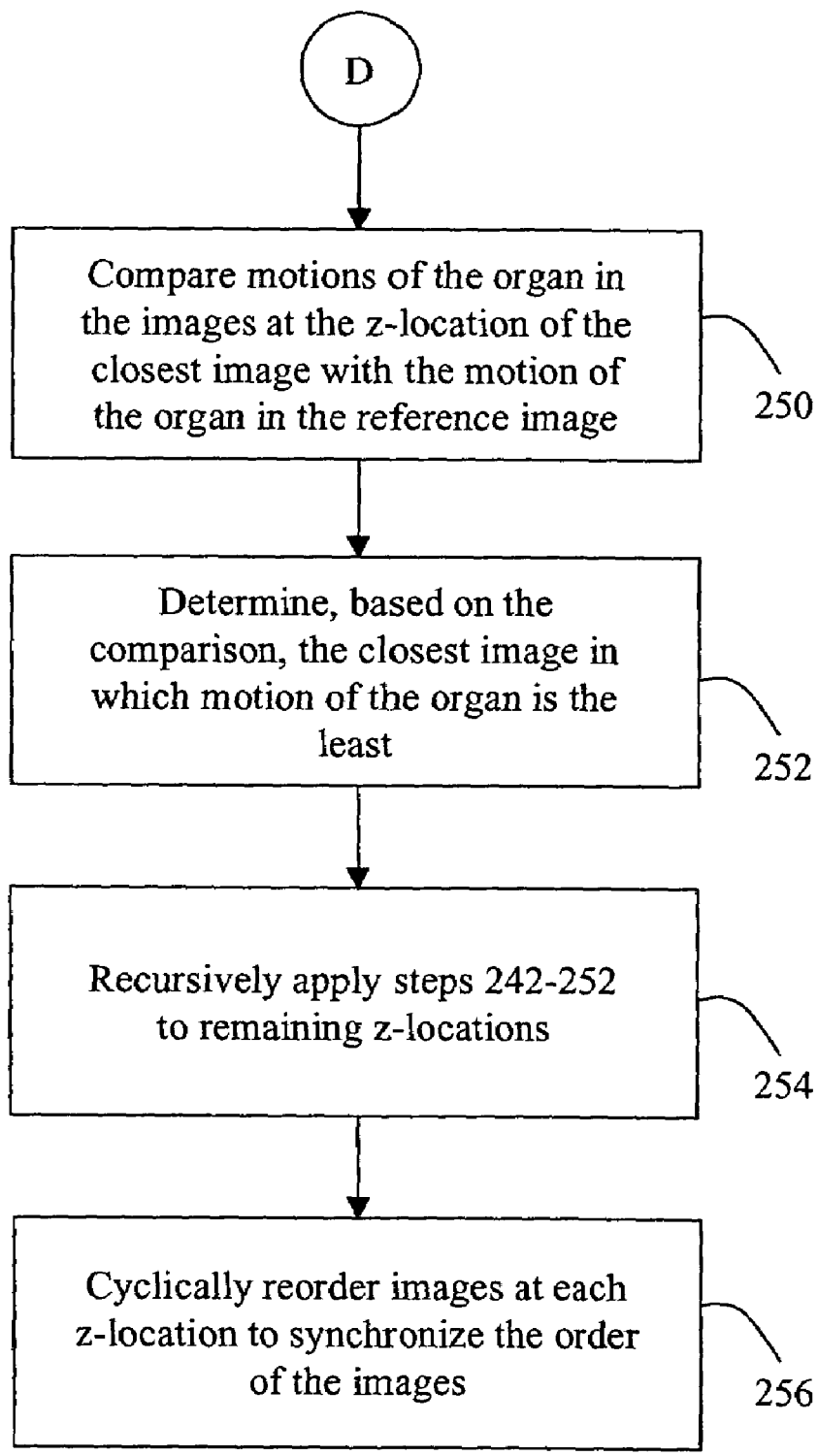
Figure 15:
FIG. 15 shows reference and closest images that are obtained during the method of FIGS. 12 and 13.
Figure 15:
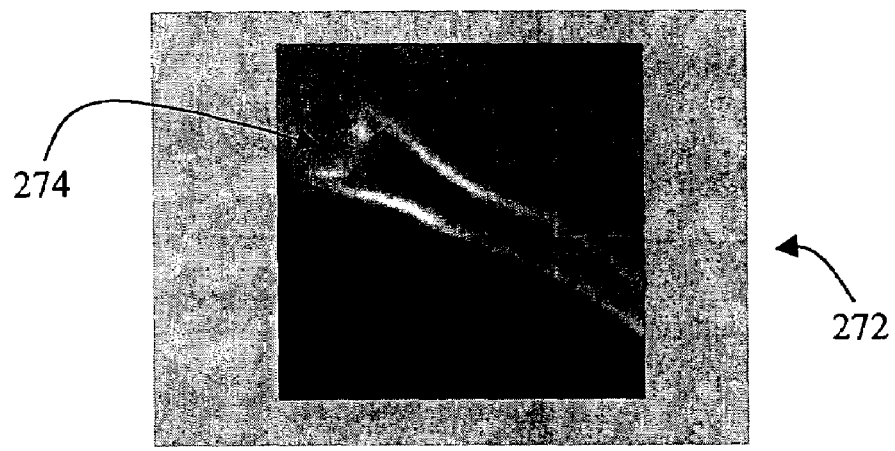
Figure 15:
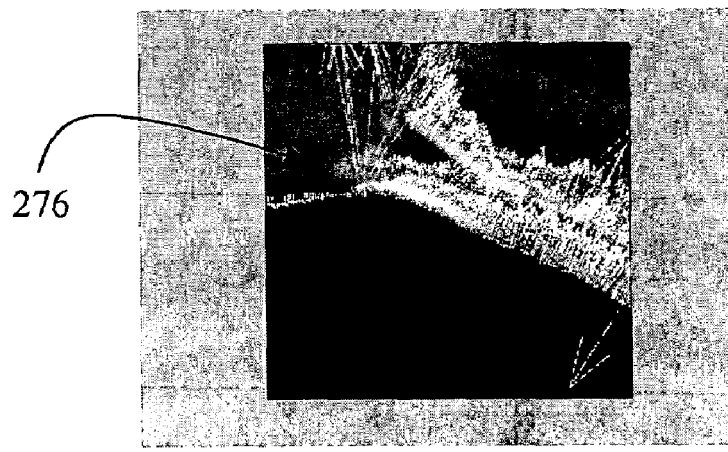

FIGS. 13, 14, and 15 show yet another alternative embodiment of the method of FIGS. 5 and 6. The method includes acquiring 240 images $I_1 \ldots I_{32}$ at multiple z-locations $z_1 \ldots z_2$ and at different times $t_1 \ldots t_4$ at each of z-locations. The method further includes designating 242 one of images $I_1 \ldots I_{16}$, for instance, $I_2$, in the temporal sequence $t_1 \ldots t_4$ at $z_{11}$ as a reference image 270. Alternatively, the method includes designating 242 one of images $I_{17} \ldots I_{32}$ in the temporal sequence $t_1 \ldots t_4$ as reference image 270. The method also includes determining a closest 2-dimensional (2D) image 272 in which motion of an organ 274, such as, for instance, a lung, of patient 22, is minimal with respect to a position of the organ in reference image 270. Closest image 272 is an image in the temporal sequence $t_1 \ldots t_n$ at a z-location, for instance, $Z_{12}$, that is adjacent the z-location of reference image 270.

Closest image 272 is determined by identifying 244 the organ boundary, shown as a white border, in reference image 270 and images, such as, for instance, $I_5 \ldots I_8$, at the z-location of closest image 272. Closest image 272 is further determined by extracting 246 normal flow vectors 276 from the organ boundary in reference image 270 and the images at the z-location of closest image 272. Extraction of normal flow vectors 276 is described in detail in S. Sirohey, A. Rosenfield, Z. Duric, "*A method of detecting and tracking irises and eyelids in video*", Pattern Recognition 35, pp. 1389-1401, 2002. Closest image 272 is also determined by fitting 248 the normal flow vectors of reference image 270 and images at the z-location of closest image 272 within an affine motion model that outputs a measure of a motion of organ 274. Closest image 272 is determined by comparing 250 motions of organ 274 in the images at the z-location of closest image 272 with the motion of organ 274 in reference image 270. Closest image 272 is further determined by determining 252 based on the comparison, closest image 272 in which the motion of organ 274 is least among the motions of organ 274 in the images at the z-location of closest image 272.

In an alternative embodiment, closest image 272 is determined by an optical flow method similar to a method described in D. Carlo, D. Metaxas, "*The integration of optical flow and deformable models with applications to human face shape and motion estimation*", Proceedings, IEEE Conference on Computer Vision and Pattern Recognition, pp. 231-238, 1996. The optical flow method is used to determine closest image 272 by determining rate of change of organ 274. In yet another alternative embodiment, closest image 272 is determined by an energy minimizing approach that is similar to a method described in A. Yuille, D. Cohen, P. Hallinan, "*Feature extraction from faces using deformable templates*", Proceedings, IEEE Computer Society Conference on Computer Vision and Pattern Recognition, pp. 104-109, 1989.

Steps 242, 244, 246, 248, 250, and 252 are recursively applied 254 to adjacent z-locations of remaining z-locations, $Z_{12}$, $Z_{13}$, $Z_{14}$, and $Z_2$. For example, steps are applied to adjacent z locations $Z_{12}$ and $z_{13}$. As another example, steps 242, 244, 246, 248, 250, and 252 are applied to adjacent z-locations $Z_{13}$ and $Z_{14}$. The method also includes cyclically reordering 256 images at the z-location of closest image 272 so that closest image 272 appears to be obtained at the same time as reference image 270. The method further includes cyclically reordering 256 images at a z-location, for instance, z-location $Z_{13}$, that is adjacent to the z-location of the closest image 272 to synchronize the order of images at the z-location adjacent to the z-location of the closest image 272 with order of the images at z-location of the closest image 272. The method includes repeating the cyclical reordering 256 for every remaining z-location in an adjacent stepwise manner. For example, the method includes cyclically reordering z-location $Z_{14}$ based on order of images at z-location $z_{13}$.

In an alternative embodiment, a method for retrospective internal gating includes comparing the cyclically reordered images that are obtained by executing the method of FIGS. 7-10 with the cyclically reordered images that are obtained by executing the method of FIGS. 13 and 14 to validate the cyclically reordered images obtained by each of the methods. The validation is performed before displaying, storing, or processing any of the cyclically reordered images.

Hence, the herein described systems and methods for retrospective internal gating use CT images with or without respiratory gating information to effectively register the CT images at or near a diaphragm of patient 22. For example, in the case of CT liver perfusion, where the arterial phase is normally measured every second in the first 30 seconds or breath hold time during which contrast injection is administered, and where the venous phase is normally measured in intervals of ten seconds with a total acquisition time up to a couple of minutes or more following the arterial phase. A challenge lies in the registration of the images acquired during the arterial phase with images acquired during the venous phase The herein described systems and methods effectively resolve the problem of registration between the images of arterial and venous phase images by providing better images regardless of whether respiratory gating information is obtained. Another extension of the herein described systems and methods is to also use a complete cycle of data during a cine acquisition mode to "degrade" the temporal resolution of each image to match with gated or nongated PET images and therefore to provide the same z-location and CT based attenuation maps having the same temporal resolution for the attenuation correction of PET emission data. If PET emission data is taken without gating, CT images from multiple phases that are combined at one z-location are used for attenuation correction so that the temporal resolution of CT images can match the temporal resolution of PET images. In certain embodiments, temporal resolution matching is utilized in PET imaging with CT based attenuation correction. If the PET emission data is taken with gating then the multiple phases of CT images can be used to correct for attenuation of the multiple phases of PET emission data. The herein described systems and methods can also be applied to oncology that requires both spatial and temporal registration of CT images for the planning of radiation therapy.

While the invention has been described in terms of various specific embodiments, those skilled in the art will recognize that the invention can be practiced with modification within the spirit and scope of the claims.

What is claimed is:

1. A method for retrospective internal gating comprising:
    acquiring images at multiple z-locations z1 . . . zn and at different times t1 . . . tn at each of the z-locations to obtain a plurality of acquired image sets, each acquired image set including only the images acquired at a single one of the z-locations;
    designating one of the images in a temporal sequence t1 . . . tn at one of the z-locations as a reference image;
    determine a closest image in which motion of an organ is minimal with respect to a position of the organ in the reference image, the closest image being an image in the temporal sequence t1 . . . tn at a z-location adjacent the z-location of the reference image; and
    reordering the images within at least one of the acquired image sets to obtain at least one synchronized image set that includes at least two images that appear to have been acquired contemporaneously, each synchronized image set including only the images acquired at a single one of the z-locations.

2. A method in accordance with claim 1 further comprising:
    extracting motion information from the images by using temporal data acquired at different times $t_1$ . . . tn at each of the z-locations.

3. A method in accordance with claim 2 wherein reordering comprises cyclically reordering the images at each of the z-locations by synchronizing the motion information to have a common starting point.

4. A method in accordance with claim 2 wherein extracting comprises:
    computing a mean intensity image from images at one of the z-locations;
    dividing the mean intensity image into a matrix of blocks of a desired size of region of interest (ROI);

generating a binary image to distinguish organs that are imaged from a background of the binary image, wherein the organs include internal organs and an outer abdominal wall;

distinguishing the internal organs from the outer abdominal wall;

selecting ROI blocks from the binary image based on a pre-determined criteria;

measuring mean intensity values at times $t_1 \ldots t_n$ for each of the selected ROI blocks, the mean intensity values measured from temporal data acquired at different times $t_1 \ldots t_n$ at the z-location at which the mean intensity image is computed; and plotting the mean intensity values as a function of times $t_1 \ldots t_n$ to provide motion information at each of the selected ROIs.

5. A method in accordance with claim 4 wherein distinguishing the internal organs from the outer abdominal wall comprises performing a segmentation process to distinguish intensities of the internal organs from intensities of the outer abdominal wall.

6. A method in accordance with claim 4 wherein distinguishing the internal organs from the outer abdominal wall comprises manually distinguishing the internal organ from the outer abdominal wall by:

depositing at least one seed in a pixel of the binary image; and appending neighboring pixels to the seed, the neighboring pixels having properties similar to that of the pixel.

7. A method in accordance with claim 4 wherein distinguishing the internal organs from the outer abdominal wall comprises automatically distinguishing the internal organs from the outer abdominal wall by connectivity and morphological operations.

8. A method in accordance with claim 4 wherein the pre-determined criteria includes whether the selected ROI blocks are above a threshold.

9. A method in accordance with claim 4 wherein the pre-determined criteria includes whether the selected ROI blocks are a part of at least one of the organs and the background.

10. A method in accordance with claim 4 wherein generating the binary image comprises generating the binary image having various intensity values to distinguish the background from the organs.

11. A method in accordance with claim 4 wherein extracting further comprises:

calculating maximas and minimas for each of the selected ROI blocks; and selecting a reference time at which there is a highest number of occurrences of at least one of the maximas and the minimas.

12. A method in accordance with claim 11 wherein extracting further comprises:

calculating at least one of a range of high points and a range of low points for each of the selected ROI blocks, wherein the range of the high points is a range of points around the maximas of the selected ROI blocks, and the range of low points is a range of points around the minimas of the selected ROI blocks; and selecting a time at which there is a highest number of occurrences of at least one of the high points and the low points.

13. A method in accordance with claim 11 further comprising:

marking all images that are scanned at the same time to designate as a reference at least one of the maximas with the highest number of occurrences and the minimas with the highest number of occurrences.

14. A method in accordance with claim 13 wherein reordering comprises choosing a common reference point at each of the z-locations.

15. A method in accordance with claim 1 wherein acquiring includes acquiring the images for a respiratory cycle of an object and at least one of a two-third and a complete gantry rotation.

16. A method in accordance with claim 1 further comprising:

designating one of the images in a temporal sequence $t_1 \ldots t_n$ at one of the z-locations as a reference image;

determining a closest image in which motion of an organ is minimal with respect to a position of the organ in the reference image, the closest image being an image in the temporal sequence $t_1 \ldots t_n$ at a z-location adjacent the z-location of the reference image.

17. A method in accordance with claim 16 wherein reordering comprises cyclically reordering images at the z-location of the closest image so that the closest image appears to be obtained at the same time as the reference image.

18. A method in accordance with claim 16 wherein determining the closest image comprises:

identifying the organ boundary in the reference images and images at the z-location of the closest image, the images at the z-location of the closest image including the closest image;

extracting normal flow vectors from the organ boundary in the reference image and the images at the z-location of the closest image;

fitting the normal flow vectors within an affine motion model that outputs a measure of a motion of the organ;

comparing motions of the organ in the images at the z-location of the closest image with the motion of the organ in the reference image; and determining based on the comparison the closest image in which the motion of the object is least among the motions of the object in the images at the z-location of the closest image.

19. A method in accordance with claim 1 wherein reordering comprises cyclically reordering a four-dimensional (4D) image set of the images based on at least one of 1-dimensional (1D) motion information of an organ that is imaged and 2-dimensional (2D) image information of the images, the cyclical reordering based on the 1D motion information providing a first set of reordered images and the cyclical reordering based on the 2-D information providing a second set of reordered images.

20. A method in accordance with claim 19 further comprising comparing the order of the first and second sets of reordered images to determine whether there is match between the orders of the first and the second sets.

21. A method in accordance with claim 1 wherein acquiring the images includes acquiring the images for one breath cycle of an object plus at least one of 0.33 seconds and 0.5 seconds.

22. A computer-readable medium encoded with a program configured to:

acquire images at multiple z-locations z1 . . . zn and at different times t1 . . . tn at each of the z-locations to obtain a plurality of acquired image sets, each acquired image set including only the images acquired at a single one of the z-locations;

extract motion information from the images by using temporal data acquired at different times t1 . . . tn at each of the z-locations and using a mean intensity value of at least a portion of one of the images;

designate one of the images in a temporal sequence t1 . . . tn at one of the z-locations as a reference image;

determine a closest image in which motion of an organ is minimal with respect to a position of the organ in the reference image, the closest image being an image in the temporal sequence t1 . . . tn at a z-location adjacent the z-location of the reference image; and reorder the images within at least one of the acquired image sets to obtain at least one synchronized image set, each synchronized image set including only the images acquired at a single one of the z-locations.

23. A computer configured to:

acquire images at multiple z-locations $z_1 \ldots z_n$ and at different times $t_1 \ldots t_n$ at each of the z-locations to obtain a plurality of acquired image sets, each acquired image set including only the images acquired at a single one of the z-locations;

designate one of the images in a temporal sequence $t_1 \ldots t_n$ at one of the z-locations as a reference image;

determine a closest image in which motion of an organ is minimal with respect to a position of the organ in the reference image, the closest image being an image in the temporal sequence $t_1 \ldots t_n$ at a z-location adjacent the z-location of the reference image; and reorder the images within at least one of the acquired image sets to obtain at least one synchronized image set, each synchronized image set including only the images acquired at a single one of the z-locations.

24. An imaging system comprising:

a scanner configured to generate attenuation data by scanning an object; and a controller electrically coupled to the scanner, the controller configured to:

acquire images at multiple z-locations z1 . . . zn and at different times t1 . . . tn at each of the z-locations to obtain a plurality of acquired image sets, each acquired image set including only the images acquired at a single one of the z-locations;

designate one of the images in a temporal sequence t1 . . . tn at one of the z-locations as a reference image;

determine a closest image in which motion of an organ is minimal with respect to a position of the organ in the reference image, the closest image being an image in the temporal sequence t1 . . . tn at a z-location adjacent the z-location of the reference image; and reorder the images within at least one of the acquired image sets to obtain at least one synchronized image set that includes at least two images that appear to have been acquired contemporaneously, each synchronized image set including only the images acquired at a single one of the z-locations.

25. A computed tomography (CT) imaging system comprising:

a radiation source;

a radiation detector; and a computer electrically coupled to the source and the detector, the computer configured to:

acquire CT images at multiple locations z1 . . . zn and at different times t1 . . . tn at each of the z-locations to obtain a plurality of acquired image sets, each acquired image set including only the CT images acquired at a single one of the z-locations;

designate one of the images in a temporal sequence t1 . . . tn at one of the z-locations as a reference image;

determine a closest image in which motion of an organ is minimal with respect to a position of the organ in the reference image, the closest image being an image in the temporal sequence t1 . . . tn at a z-location adjacent the z-location of the reference image; and reorder the CT images within at least one of the acquired image sets to obtain at least one synchronized image set that includes at least two images that appear to have been acquired contemporaneously, each synchronized image set including only the CT images acquired at a single one of the z-locations.

* * * * *